US009993785B2

United States Patent
Morrissey et al.

(10) Patent No.: US 9,993,785 B2
(45) Date of Patent: Jun. 12, 2018

(54) 2D LOW LEVEL MIXING BAG FOR STORAGE AND SHIPPING

(71) Applicant: EMD Millipore Corporation, Burlington, MA (US)

(72) Inventors: Martin Morrissey, Burlington, MA (US); Brian Pereira, Burlington, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days. days.

(21) Appl. No.: 15/791,869

(22) Filed: Oct. 24, 2017

(65) Prior Publication Data

US 2018/0043322 A1    Feb. 15, 2018

Related U.S. Application Data

(62) Division of application No. 15/658,503, filed on Jul. 25, 2017, now Pat. No. 9,827,541, which is a division
(Continued)

(51) Int. Cl.
*B01F 15/00* (2006.01)
*C12M 1/00* (2006.01)
(Continued)

(52) U.S. Cl.
CPC ...... *B01F 15/0085* (2013.01); *B01F 7/00241* (2013.01); *B01F 13/0827* (2013.01);
(Continued)

(58) Field of Classification Search
CPC .................................................. B01F 15/0085
See application file for complete search history.

(56) References Cited

U.S. PATENT DOCUMENTS 5,141,327 A * 8/1992 Shiobara ............. B01F 13/0827
366/127
5,366,698 A * 11/1994 Smith ................ B01D 21/2438
261/91
(Continued)

FOREIGN PATENT DOCUMENTS

EP    2336051 A1    6/2011
GB    2202549 A    9/1988
(Continued)

OTHER PUBLICATIONS

International Search Report/Written Opinion dated Apr. 22, 2014 in corresponding PCT application No. PCT/US2013/068375.
(Continued)

*Primary Examiner* — Abbas Rashid
(74) *Attorney, Agent, or Firm* — Nields, Lemack & Frame, LLC

(57) ABSTRACT

A disposable container, such as a deformable bag, for a fluid, having one or more inlets and one or more outlets and an impeller assembly within the container to cause mixing, dispersing, homogenizing and/or circulation of one or more ingredients contained or added to the container. The region within the container that can contain liquid is funnel shaped, which allows very low fluid level mixing, dispensing while mixing, and a reduction or elimination of vortex formation.

6 Claims, 4 Drawing Sheets

Related U.S. Application Data of application No. 14/440,376, filed as application No. PCT/US2013/068375 on Nov. 5, 2013, now Pat. No. 9,744,507.

(60) Provisional application No. 61/731,129, filed on Nov. 29, 2012.

(51) Int. Cl.
    *B01F 7/00*     (2006.01)
    *C12M 1/06*     (2006.01)
    *B01F 13/08*     (2006.01)

(52) U.S. Cl.
    CPC ....... *B01F 15/00487* (2013.01); *C12M 23/14* (2013.01); *C12M 27/02* (2013.01); *B01F 2215/0034* (2013.01); *B01F 2215/0073* (2013.01)

(56) References Cited

U.S. PATENT DOCUMENTS

| | | | |
|---|---|---|---|
| 5,650,100 A | 7/1997 | Just | |
| 5,941,635 A * | 8/1999 | Stewart | B01F 5/0068 366/165.5 |
| 6,981,794 B2 * | 1/2006 | Bibbo | A61L 2/02 366/149 |
| 7,153,021 B2 * | 12/2006 | Goodwin | B01F 13/0818 366/273 |
| 7,278,780 B2 | 10/2007 | Goodwin et al. | |
| 7,377,686 B2 | 5/2008 | Hubbard | |
| 7,384,783 B2 | 6/2008 | Kunas et al. | |
| 7,481,572 B2 | 1/2009 | Terentiev | |
| 7,879,599 B2 * | 2/2011 | Goodwin | C12M 23/14 435/289.1 |
| 7,972,058 B2 * | 7/2011 | Furey | B01F 11/0071 366/275 |
| 8,678,638 B2 * | 3/2014 | Wong | B01F 7/162 366/142 |
| 9,101,893 B1 * | 8/2015 | Pavlik | B01F 15/00155 |
| 9,744,507 B2 | 8/2017 | Morrissey et al. | |
| 9,827,541 B1 | 11/2017 | Morrissey et al. | |
| 2003/0226857 A1 * | 12/2003 | Bibbo | A61L 2/02 222/148 |
| 2003/0227817 A1 | 12/2003 | Martel et al. | |
| 2005/0237853 A1 | 10/2005 | Martel et al. | |
| 2006/0240546 A1 | 10/2006 | Goodwin et al. | |
| 2007/0253286 A1 * | 11/2007 | Huang | B01F 7/00208 366/273 |
| 2007/0253287 A1 | 11/2007 | Myhrberg et al. | |
| 2010/0046323 A1 * | 2/2010 | Tien | B01F 13/0818 366/274 |
| 2010/0282685 A1 | 11/2010 | Halaka et al. | |
| 2011/0013473 A1 | 1/2011 | Ludwig et al. | |
| 2011/0158037 A1 | 6/2011 | Bernard et al. | |
| 2012/0027324 A1 | 2/2012 | Morrissey et al. | |
| 2012/0208039 A1 | 8/2012 | Barbaroux et al. | |
| 2013/0088933 A1 * | 4/2013 | Yum | B01F 1/00 366/147 |
| 2015/0118753 A1 | 4/2015 | Brau et al. | |
| 2015/0258513 A1 | 9/2015 | Morrissey et al. | |
| 2017/0320027 A1 | 11/2017 | Morrissey et al. | |

FOREIGN PATENT DOCUMENTS

| | | | | |
|---|---|---|---|---|
| JP | 56-156748 U | | 11/1981 | |
| JP | 7-3717 U | | 1/1995 | |
| JP | 2004-149153 A | | 5/2004 | |
| JP | 2007-276881 A | | 10/2007 | |
| JP | 2012-170364 A | | 9/2012 | |
| WO | WO-2011112680 A1 * | | 9/2011 | B01F 7/162 |

OTHER PUBLICATIONS

International Preliminary Report on Patentability dated Jun. 18, 2015 in corresponding PCT application No. PCT/US2013/068375.

Japanese communication, with English translation, dated May 31, 2016 in corresponding Japanese patent application No. 2015-545054.

Japanese communication, with English translation, dated Feb. 7, 2017 in corresponding Japanese patent application No. 2015-545054.

Japanese communication, with English translation, dated Aug. 29, 2017 in corresponding Japanese patent application No. 2015-545054.

European communication dated Jul. 15, 2016 in corresponding European patent application No. 13858238.2.

* cited by examiner

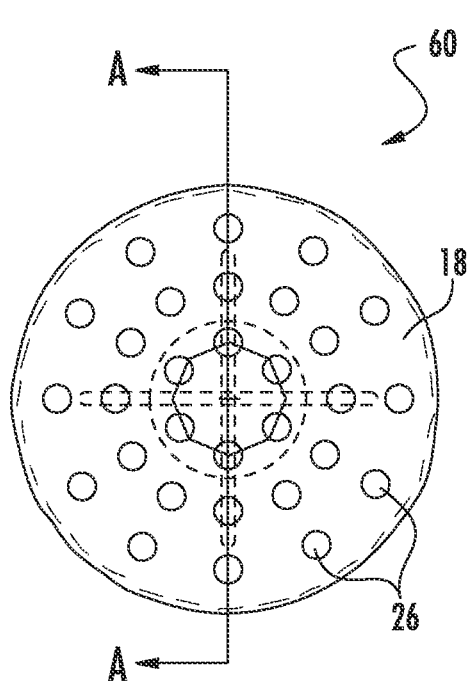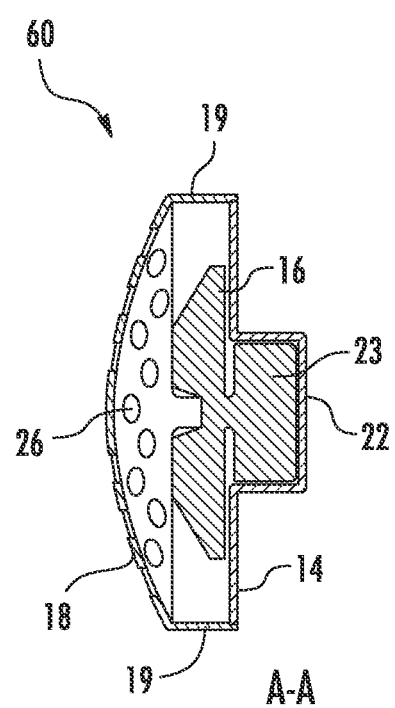
FIG. 3
FIG. 4

2D LOW LEVEL MIXING BAG FOR STORAGE AND SHIPPING

This application is a divisional of U.S. patent application Ser. No. 15/658,503 filed Jul. 25, 2017, which is a divisional of U.S. patent application Ser. No. 14/440,376 filed May 4, 2015 (now U.S. Pat. No. 9,744,507 issued Aug. 29, 2017), which is a 371 of PCT/US2013/068375 filed Nov. 5, 2013, which claims priority of U.S. Provisional Application Ser. No. 61/731,129 filed Nov. 29, 2012, the disclosures of which are incorporated herein by reference in their entirety.

FIELD

The embodiments disclosed herein relate to a disposable 2D container and impeller assembly, the impeller assembly preferably being magnetically driven and coupled to the container.

BACKGROUND

Traditionally, fluids have been processed in systems that utilize stainless steel containers. These containers are sterilized after use so that they can be reused. The sterilization procedures are expensive and cumbersome as well as being ineffectual at times.

In order to provide greater flexibility in manufacturing and reduce the time needed to effect a valid regeneration of the equipment, manufacturers have begun to utilize disposable sterilized bags that are used once with a product batch and then disposed.

An example of use of these disposable bags is in a system for mixing two or more ingredients, at least one of which is liquid and the other(s) being liquid or solid and the bag has a means for causing the ingredients to mix as uniformly as possible.

For example, in the production of vaccines, the liquids involved often contain aluminum salt as an adjuvant. The aluminum salt improves the effectiveness of the vaccine by enhancing the body's immune response. Unfortunately, the aluminum salt has particles sizes larger than 0.2 µm, and thus sterile filtering generally is not an option. As a result, it is often advantageous to minimize the number of containers into which the vaccine needs to be transferred, since each transfer represents a potential breach of sterility, and the resulting contamination can't be filtered away. Accordingly, it is advantageous to be able to mix vaccines in the same container, such as a flexible, disposable bag, that they are shipped in.

Another example is a bioreactor or fermentor in which cells are either in suspension or on microcarriers and the bag has a means for circulating the liquid, gases and in some cases the cells around the interior of the bag.

Most conventional mixing bags are shaped like cylinders, with the bottom of the bag forming a cone, to mimic the shape of the tanks that the disposable bags are replacing. Although this shape is conducive to mixing the contents of the bag, it is not conducive to shipping and storage.

Other conventional mixing bags are shaped like cubes. The cube shape is conducive to shipping and storage, but is not a good shape for mixing, as the corners of the cube easily can become dead spots where mixing is impeded.

Typically, the means for mixing or circulating is a magnetically coupled impeller contained within the bag and a magnetic motor outside the bag which remotely causes the impeller to spin.

It therefore would be desirable to provide a disposable, preferably deformable, container for fluids that is conducive to mixing, shipping and storage. It also would be desirable to form a flat, 2D bag made from two pieces of film bonded together to form a funnel-shape and an integral impeller assembly located towards the bottom of the funnel. The flat nature of the bag is conducive to shipping and storage in an empty or full state.

SUMMARY

In accordance with certain embodiments, disclosed herein is a disposable container, such as a deformable bag, for a fluid, the container having one or more inlets and one or more outlets and one or more impeller assemblies within the container to cause mixing, dispersing, homogenizing and/or circulation of one or more ingredients contained or added to the container. In accordance with certain embodiments, the region within the interior of the disposable container that can contain liquid and in which liquid is introduced is delimited by liquid impermeable seams sealingly adjoining walls of the container. In accordance with certain embodiments, the region within the interior of the disposable container that can contain liquid and into which liquid is introduced is angled in the shape of a funnel, where the small end of the funnel is proximate the outlet of the container.

Also disclosed is a system for mixing ingredients in a container, the system comprising a 2D container having a mixing region that is shaped to minimize or eliminate dead spot regions, one or more impeller assemblies, and one or more drives for the impeller assembly or assembly. In accordance with certain embodiments, the mixing region is delimited by liquid impermeable seams sealingly adjoining walls of the container. In accordance with certain embodiments, the mixing region is funnel-shaped. In accordance with certain embodiments, an outlet of the container is at the narrowest region of the funnel shape.

Also disclosed is a method of mixing ingredients in a disposable container with one or more impeller assemblies disposed in the container. The method includes introducing ingredients to be mixed into a container, wherein one or more impeller assemblies is at least partially contained in and is sealed in the container, and driving the blades or vanes of the impeller assembly or assemblies to agitate the ingredients in the bag. The ingredients occupy a shaped region in the bag that minimizes or eliminates dead spots. Preferably the shaped region is funnel-shaped. In certain embodiments, the driver(s) for the impeller assembly or assemblies is external to the bag, and the impeller assembly or assemblies is driven magnetically. In certain embodiments, at least one of the ingredients to be mixed is a liquid.

Also disclosed is a liquid processing system which comprises a disposable container having one or more inlets and one or more outlets and one or more impeller assemblies within the container to cause mixing, dispersing, homogenizing and/or circulation of one or more ingredients contained or added to the container, and a tangential flow filtration unit and conduits to effect flow from the container to the tangential flow filtration unit and back to the container. The ingredients occupy a shaped region in the bag that minimizes or eliminates dead spots. Preferably the shaped region is funnel-shaped.

The funnel shape directs any settling solids back to the impeller assembly, where they are re-agitated. The funnel-shape also improves drainability out of the container.

BRIEF DESCRIPTION OF THE DRAWINGS

FIG. 3 is a top view of a mixing element in accordance with certain embodiments;

FIG. 4 is a cross sectional view of the mixing element taken along line A-A of FIG. 3.

DETAILED DESCRIPTION OF SPECIFIC EMBODIMENTS

In accordance with certain embodiments, the disposable container designed to receive and hold ingredients can be formed of monolayer or multilayer flexible walls formed of a polymeric composition such as polyethylene, including ultrahigh molecular weight polyethylene, linear low density polyethylene, low density or medium density polyethylene; polypropylene; ethylene vinyl acetate (EVOH); polyvinyl chloride (PVC); polyvinyl acetate (PVA); ethylene vinyl acetate copolymers (EVA copolymers); blends of various thermoplastics; co-extrusions of different thermoplastics; multilayered laminates of different thermoplastics; or the like. By "different" it is meant to include different polymer types such as polyethylene layers with one or more layers of EVOH as well as the same polymer type but of different characteristics such as molecular weight, linear or branched polymer, fillers and the like. Typically medical grade and preferably animal-free plastics are used. They generally are sterilizable such as by steam, ethylene oxide or radiation such as beta or gamma radiation. Most have good tensile strength, low gas transfer and are either transparent or at least translucent. Preferably the material is weldable and is unsupported. Preferably the material is clear or translucent, allowing visual monitoring of the contents. The container can be provided with one or more inlets, one or more outlets and one or more optional vent passages. One or more impeller assemblies can be positioned in the container for mixing the container contents.

In certain embodiments, the container may be a disposable, deformable, foldable bag that defines a volume, that is sterilizable for single use, capable of accommodating contents, such as biopharmaceutical liquids, and that can accommodate one or more mixing devices partially or completely within the interior of the container. The volume can be a closed volume that can be opened, such as by suitable valving, to introduce a liquid into the volume, and to dispense liquid therefrom, such as after mixing is complete.

The container is preferably a two dimensional (2D) or "pillow" bag, formed by joining two or more sheets of material (or a single sheet to itself) in sealing relation. Preferably it is a single-use container.

Figure 1:
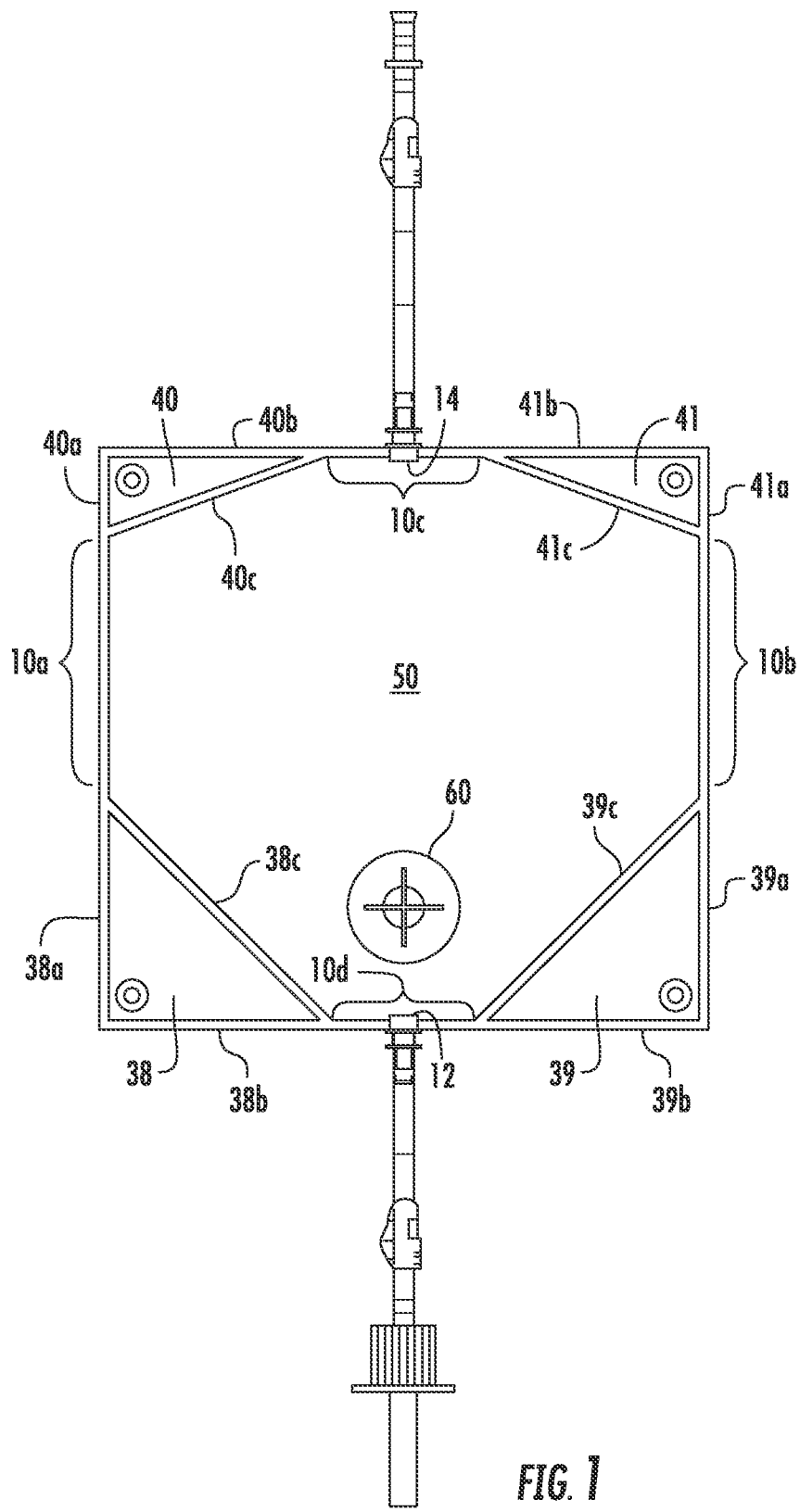
FIG. 1 is a schematic view of a disposable container in accordance with certain embodiments.

In accordance with certain embodiments, portions of the container can be sealed such as by welding to create regions where no liquid is present and where no liquid can flow, thereby modifying the shape of the volume of the container that receives liquid to be mixed. An example is shown in FIG. 1, where a funnel-shaped container is formed from initially rectangular sheets of material. Those skilled in the art will appreciate that other initial material shapes can be used to form the final desired funnel-shape. The lower left and right corner triangular regions 38, 39 of the container 10 are sealed and are not in fluid communication with an inlet 12 or outlet 14, and therefore contain no ingredients to be mixed. Similarly, optionally upper left and right corner triangular regions 40, 41 of the container are sealed and are not in fluid communication with an inlet or outlet, and therefore contain no ingredients to be mixed.

More specifically, in accordance with certain embodiments, region 38, which is sealed from and not in fluid communication with mixing region 50, is defined by the container sealed end walls 38a, 38b, and by interior sealed wall 38c. Region 39, which is sealed from and not in fluid communication with mixing region 50, is defined by the container sealed end walls 39a, 39b, and by interior sealed wall 39c. Interior sealed wall 38c is angled, such as about a 45° angle, relative to end wall 38a and end wall 38b. Interior sealed wall 39c is angled, such as about a 45° angle, relative to end wall 38a and end wall 38b. Other angles, such as angles from about 22.5° to about 60°, also are acceptable. These two walls thus create a region 50 that is tapered toward the outlet 12.

Optionally region 40, which is sealed from and not in fluid communication with mixing region 50, is defined by the container sealed end walls 40a, 40b, and by interior sealed wall 40c. Optionally region 41, which is sealed from and not in fluid communication with mixing region 50, is defined by the container sealed end walls 41a, 41b, and by interior sealed wall 41c.

The sealing of walls can be carried out by welding using heat to melt and fuse or bond the material as is known in the art. Alternatively, the bag could be blow molded or the walls could be adhered together with an adhesive.

Accordingly, ingredients introduced into the container can occupy only the mixing volume 50 defined by container sealed walls 38c and 39c (and optionally sealed walls 40c and 40d), and container end walls 10a (between end wall 40a and 38a), 10b (between end wall 39a and 41a), 10c (between end wall 41b and 41b), and 10d (between end wall 38b and 39b).

In view of the shape of the region 50, the introduction of fluid into the region 50 causes the container 10 to expand to an elliptical shaped cross-section. This closely mimics a 3D bag.

Figure 5:
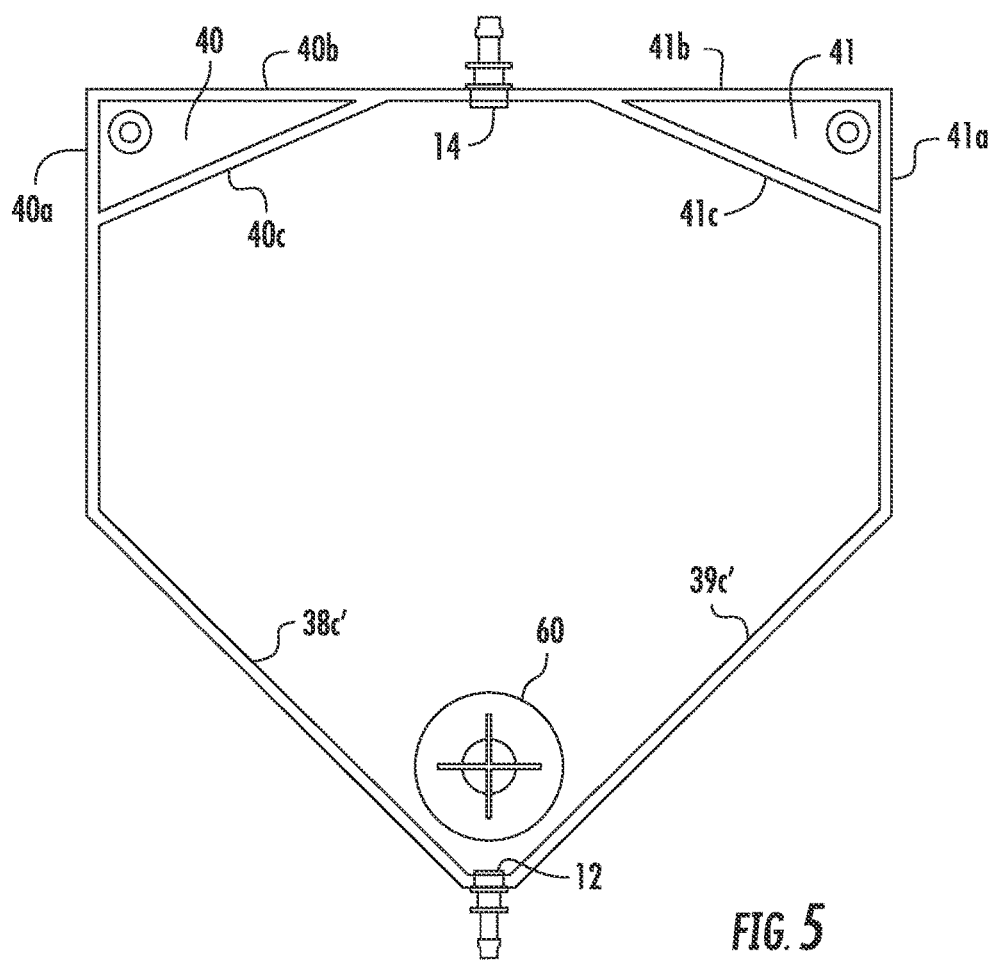
FIG. 5 is a schematic view of a disposable container in accordance with an alternative embodiment.

In accordance with certain embodiments, the sheet or sheets used to form the container can initially be shaped in a funnel-shape, as shown in FIG. 5, such as by cutting rectangular sheets to form a funnel shape. The perimeter walls of the funnel-shaped sheets (e.g., 38c' and 39c') can then be sealed to one another to form the funnel-shaped 2D bag. In the embodiment shown in FIG. 5, the upper left region 40 and upper right region 41 are formed as in the embodiment of FIG. 1, although these could also be pre-cut in the desired shape, thereby eliminating the regions 40 and 41. A hard bottomed (funnel) bag with a flexible wall also could be used.

The container 10 contains, either partially or completely within its interior, one or more impeller assemblies 60 for mixing or circulating the ingredients contained in the mixing region 50 of the container 10. The impeller assembly can be made of a suitable plastic material, such as polyethylene, that does not react or otherwise interfere with the intended liquid contents of the container. In accordance with certain embodiments, each impeller assembly includes one or more blades, which are movable, such as by rotation or oscillation about an axis. The number and shape of the blades is not particularly limited, provided they provide sufficient agitation of the fluid within the container when actuated. The blade or blades may also be constructed of plastic material, such as polyethylene, or any polymer resistant to gamma irradiation, such as a polypropylene co-polymer. In certain embodiments, the impeller assembly 60 converts rotational motion into a force that mixes the fluids it is in contact with.

Preferably an impeller assembly 60 is located in proximity to the bottom of the container, preferably centrally located with respect to the longitudinal centerline of the container 10. Placing the impeller assembly 60 near the bottom of the funnel shape allows for mixing even at very low liquid levels in the container 10, and allows for mixing to continue during dispensing. Preferably the impeller assembly is as close to the bottom of the container as possible, limited by the size of the impeller assembly. Having it as close to the bottom of the container as possible allows the impeller to keep mixing for as long as possible until the fluid level is broken by the rotating blades. The resulting container can mix 1/10 of its full volume, and have its impeller remain completely submerged in the process liquid. This allows mixing at low liquid levels without splashing or foam generation, ensures complete drainability, and allows the bag to actively mix while dispensing, even at a very low (about 1/10 the capacity of the bag) levels of liquid in the bag.

In certain embodiments, the impeller assembly 60 has a magnetic base, such as a mixing impeller overmolded magnet. In certain embodiments, when the impeller assembly 60 is installed in the container 10, the magnetic base protrudes outside the container 10, with the remainder of the impeller assembly 60 is housed inside the container 10. The driver 62 (e.g., a magnetic driver) for the impeller assembly is external to the container 10.

In accordance with certain embodiments, the impeller assembly 60 has a protective hood 18 surrounding at least a portion of the moveable blades or vanes 16 of the impeller assembly and being above at least a portion of the blades or vanes 16, as shown in FIGS. 3 and 4. In accordance with certain embodiments, the hood 18 surrounds the blades or vanes 16 and arcs over the height of the blades or vanes. Even more particularly, in certain embodiments the hood 18 is shaped in a dome shape or semi-spherical shape that is around and above the impeller blades. The hood 18 has one or more, preferably, two or more openings to allow for good liquid circulation when the blades are in motion. The hood acts as a protector for the container surface against the impeller assembly both during shipping and storage as well as when in use, particularly at lower liquid levels. In addition, the hood can, in some embodiments, act as a vortex breaker especially at lower liquid levels so as to prevent foaming and to increase turbulence and therefore mixing efficiency.

In certain embodiments, the protective hood 18 is coupled to the base with one or more ribs or legs 19. Where a plurality of ribs 19 is used, preferably they are equally spaced. The open regions between spaced ribs 19 are generally normal to the axis about which the impeller blades rotate, and provide fluid access to the interior of the impeller assembly. The number and shape of the blades 16 is not particularly limited, provided they provide sufficient agitation of the fluid within the container when actuated. The base 14 and hood 18 define a housing for the moveable blade or blades, and can be made of a suitable plastic material such as polyethylene, that does not react or otherwise interfere with the intended liquid contents of the container. The blade or blades may also be constructed of plastic material, such as polyethylene, or any polymer resistant to gamma irradiation, such as a polypropylene co-polymer.

The top surface of the hood 18 should be smooth to avoid damaging the container upon contact with the hood. In certain embodiments, the top surface of the hood 18 includes a plurality of spaced apertures 26 formed therein, to allow fluid passage to and from the interior of the impeller assembly 60. In the embodiment shown in FIG. 3, a first ring of spaced apertures is located near the outer circumferential edge of the top surface, a second ring of spaced apertures is located radially inwardly of the first ring, and a third ring of apertures is located radially inwardly of the second ring. In the embodiment shown in FIG. 3, the first ring of spaced apertures includes twelve apertures; the second ring of spaced apertures includes twelve apertures, and the third ring of spaced apertures includes six apertures. Those skilled in the art will appreciate that the particular number and pattern of apertures is not limited to the embodiment shown in FIG. 3. Although in the embodiment shown, each aperture within a ring is equally sized and is generally circular, the shape and diameter of the apertures is not limited. The apertures can be formed by a variety of means, such as by drilling.

Preferably the hood is dome shaped to protect the container, and the assembly has side openings to pull liquid in, and openings in the hood to propel liquid out. In general, the amount of open area in the hood is a trade-off between the ability of the hood to protect the bag from damage, and the mixing efficiency of the impeller assembly. For the unit to work efficiently, it needs to be able to pull fluid in from the side openings in the hood (i.e. the spaces between the legs). It also needs to be able to propel the fluid out through the top (hence the need for the apertures in the hood). The more open area on top, the better the mixing efficiency. However, if the size of the apertures is too large, the container material could sag through them and touch the impeller, damaging the container.

The container 10 may contain one or more inlets 12 and outlets 14 and optionally other features such as sterile gas vents (not shown) and ports (not shown) for the sensing of the liquid within the container for parameters such as conductivity, pH, temperature, dissolved gases and the like. Those skilled in the art will appreciate that although element 12 is labeled an inlet and element 14 is labeled an outlet, these could be reversed so that element 12 is the outlet and element 14 is the inlet, or they each could function as both inlets and outlets.

In one embodiment, the disposable container is positioned within a solid support container for ease of filling and emptying the container of fluid.

Figure 2:
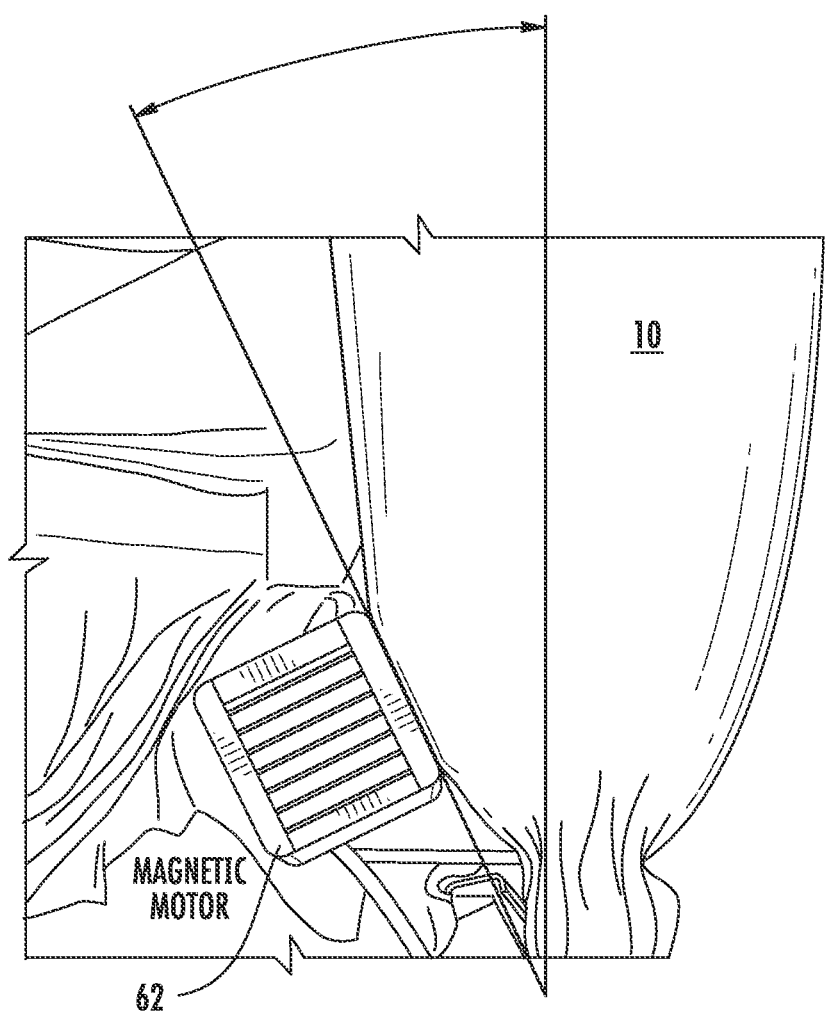
FIG. 2 is a photograph of a filled disposable container being mixed in accordance with certain embodiments.

FIG. 2 illustrates the elliptical shape of the container 10 when filled, and shows the external magnetic motor drive 62 and the impeller assembly 60 positioned at an angle "X" relative to the longitudinal centerline of the container 10. The angle of the impeller assembly causes a line normal to the impeller assembly to be directed to the opposite face of the container 10, which reduces or eliminates the formation of a vortex, and increases turbulence and mixing efficiency. This is particularly desirable when processing shear or oxygen-sensitive proteins.

What is claimed is:

1. A method of mixing ingredients in a disposable container comprising a deformable, foldable bag of flexible material defining a bag volume and having a first surface and an opposite facing second surface, wherein portions of said first and second surfaces are welded together to form at least one seal in the form of a wall separating a fluid-receiving region in said bag volume from one or more non-fluid receiving regions in said bag volume, one or more inlets in said container in fluid communication with said fluid-receiving region, and one or more outlets in said container in fluid communication with said fluid-receiving region, wherein said one or more non-fluid receiving regions is triangular shaped such that said fluid-receiving region is tapered towards the one or more outlets; said disposable container having one or more impeller assemblies mounted at least partially within said fluid-receiving region of said deformable, foldable bag, said method comprising introducing said ingredients to be mixed into said container, driving said one or more impeller assemblies to agitate said ingredients, wherein said ingredients occupy said fluid-receiving region in the bag which minimizes or eliminates dead spots.

2. The method of claim 1, wherein said one or more impeller assemblies comprises movable blades and a hood surrounding at least a portion of said movable blades.

3. The method of claim 1, wherein said one or more impeller assemblies is mounted near said one or more outlets.

4. A method of mixing ingredients in a disposable container, said disposable container comprising:
   a deformable, foldable 2D bag of flexible material defining a bag volume and a first surface and an opposite facing second surface; one or more inlets in said container; one or more outlets in said container; wherein first portions of said first and second surfaces are welded together to form at least one seal in the form of a wall separating a fluid-receiving region in said 2D bag volume from one or more non-fluid receiving regions in said 2D bag volume; second portions of said first and second surfaces are welded together to form a tapered region that tapers towards said one or more outlets in said container; wherein said one or more non-fluid receiving regions is triangular shaped; one or more impeller assemblies mounted at least partially within said fluid-receiving region;
   said method comprising introducing said ingredients to be mixed into said container and driving said one or more impeller assemblies to agitate said ingredients, wherein said ingredients occupy said fluid-receiving region in the bag which minimizes or eliminates dead spots.

5. The method of claim 4, wherein said one or more impeller assemblies comprises movable blades and a hood surrounding at least a portion of said movable blades.

6. The method of claim 4, wherein said one or more impeller assemblies is mounted near said one or more outlets.

* * * * *